(12) United States Patent
Rührnschopf

(10) Patent No.: US 7,551,716 B2
(45) Date of Patent: **\*Jun. 23, 2009**

(54) APPARATUS AND METHOD FOR SCATTER CORRECTION IN PROJECTION RADIOGRAPHY

(75) Inventor: Ernst-Peter Rührnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 181 days.

This patent is subject to a terminal disclaimer.

(21) Appl. No.: 11/629,571

(22) PCT Filed: Jun. 14, 2005

(86) PCT No.: PCT/EP2005/052744

§ 371 (c)(1),
(2), (4) Date: Dec. 14, 2006

(87) PCT Pub. No.: WO2005/124683

PCT Pub. Date: Dec. 29, 2005

(65) Prior Publication Data

US 2008/0013673 A1    Jan. 17, 2008

(30) Foreign Application Priority Data

Jun. 16, 2004   (DE)   ................ 10 2004 029 010

(51) Int. Cl.
*G01N 23/04*   (2006.01)
(52) U.S. Cl. .................... 378/62; 378/37; 378/87; 378/98.4
(58) Field of Classification Search ............. 378/62, 378/98.4, 901, 86, 87, 37; 382/132
See application file for complete search history.

(56) References Cited

U.S. PATENT DOCUMENTS

| 5,168,161 | A | 12/1992 | Markandey |
| 5,440,647 | A | 8/1995 | Floyd, Jr. et al. |
| 6,104,777 | A | 8/2000 | Darboux et al. |
| 7,308,072 | B2 * | 12/2007 | Ruhrnschopf ............ 378/7 |
| 2002/0141541 | A1 | 10/2002 | Darboux et al. |
| 2005/0249431 | A1 | 11/2005 | Ruhrnschopf |
| 2006/0008046 | A1 | 1/2006 | Ruhrnschopf |

FOREIGN PATENT DOCUMENTS

DE        3826285 A1    1/1990

OTHER PUBLICATIONS

M.Darboux, J.M.Dinten Physical model based scatter correction in mammography, Proc. SPIE; 1997, pp. 405-410, vol. 3032.
J.M.Dinten; J.M.Volle Physical model based restoration of mammographies, Proc. SPIE; 1998, pp. 641-650, vol. 3336.
W. Kalender Monte Carlo calculations of x-ray scatter data for diagnostic radiology, Phys.Med.Biol. 1981, pp. 835-849, vol. 26. No. 5.

(Continued)

*Primary Examiner*—Jurie Yun

(57) ABSTRACT

An apparatus for projection radiography is set up for correcting stray radiation. The apparatus comprises an evaluation unit which evaluates the distribution of stray radiation, which is arranged in a tabular manner in a data memory, for correcting stray radiation, said distribution being initially determined with the aid of Monte-Carlo-Simulation which takes into account multiple interactions of the photons with the object which is to be analyzed.

19 Claims, 3 Drawing Sheets

OTHER PUBLICATIONS

Abbott et al Image deconvolution as an aid to mammographic artefact identification I basic techniques, Proc. SPIE, 1999, pp. 698-709, vol. 3661.

K.Nykanen et al X-ray scattering in full field digital mammography, Med.Phys., Jul. 2003, pp. 1864-1873. vol. 30 (7).

Trotter et al Thickness-dependent Scatter-Correction Algorithm for Digital Mammography, Proc. SPIE, 2002, pp. 469-478, vol. 4682.

Baydush et al Improved image quality in digital mammography with image processing, Med.Phys. Jul. 2000, pp. 1503-1508, vol. 27, No. 7.

Seibert et al X-ray scatter removal by deconvolution, Med.Phys., 1988, pp. 567-575, vol. 15.

Andreo Pedro, "Monte Carlo techniques in medical radiation physics", Phys. Med. Biol., [Online], vol. 36, No. 7, 1991, pp. 861-920, XP002379412, IOP Publishing Ltd., UK, Retrieved from Internet: URL:ej.iop.org/links/q56/AJcWwAeYggjKo01mKVC1Aw/pb910701.pdf> [Retrieved from Internet: May 3, 2006].

Qi Jinyi and Ronald H. Huesman, "Scatter correction for positron emission mammography", Physics in Medicine and Biology, [Online], vol. 47, 2002, pp. 2759-2771, XP002379413, Institute of Physics Publishing Ltd., UK, Retrieved from Internet: URL:ej.iop.org/links/q43/9lrd2jt8jODMYiysEFIGZg/m21515.pdf, Retrieved on May 3, 2006.

* cited by examiner

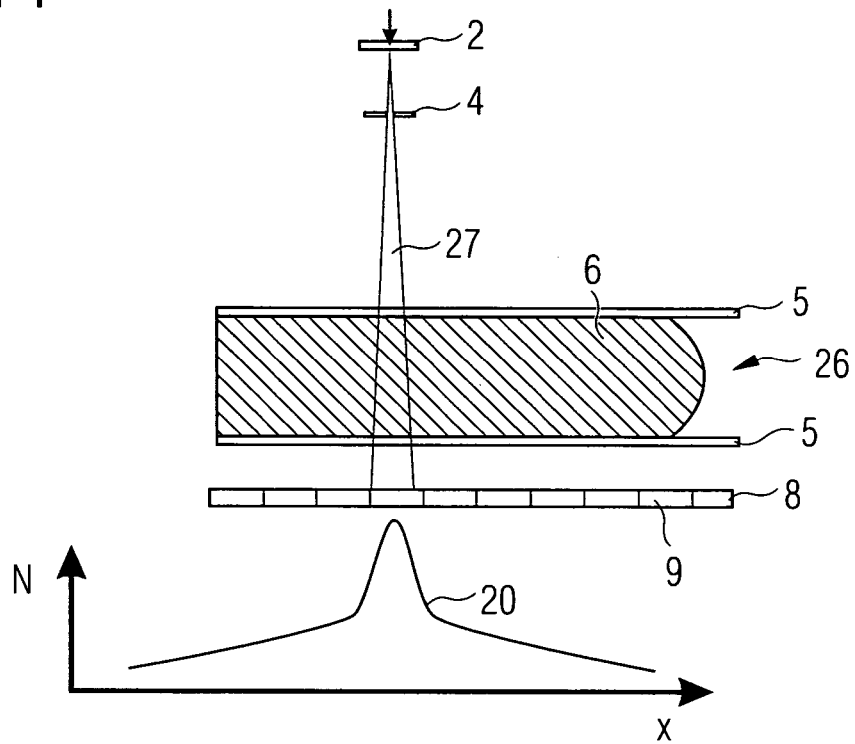
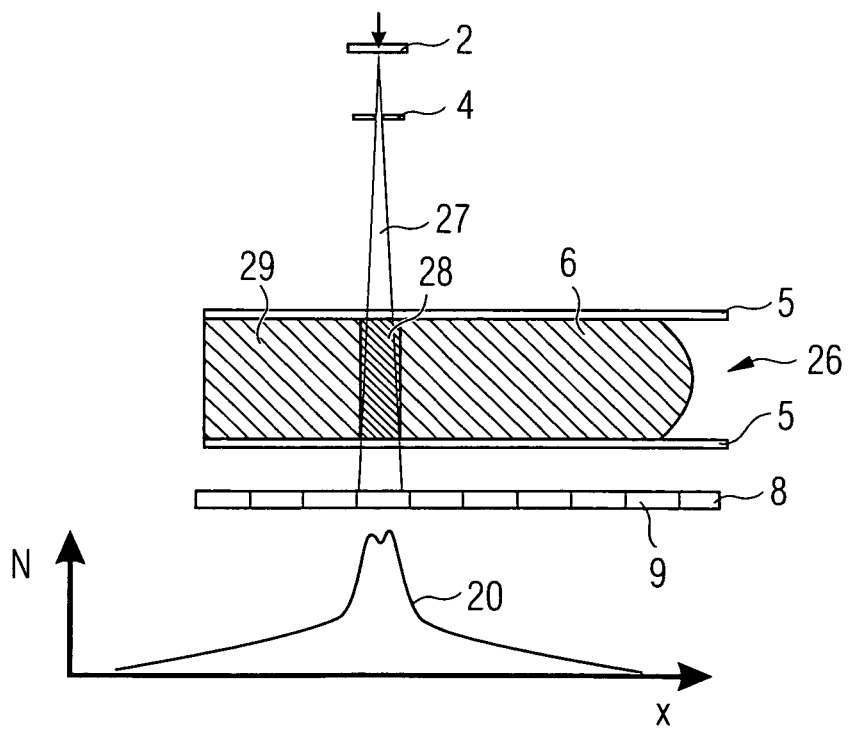

APPARATUS AND METHOD FOR SCATTER CORRECTION IN PROJECTION RADIOGRAPHY

CROSS REFERENCE TO RELATED APPLICATIONS

This application is the U.S. National Stage of International Application No. PCT/EP2005/052744, filed Jun. 14, 2005 and claims the benefit thereof. The International Application claims the benefits of German application No. 10 2004 029 010.5 DE filed Jun. 16, 2004, both of the applications are incorporated by reference herein in their entirety.

FIELD OF INVENTION

The invention relates to an apparatus for projection radiography comprising a radiation source, a detector and, downstream of said detector, a processing unit which uses the projection data supplied by the detector to approximately determine the scatter material distribution of the object under examination and which reads out scatter information from a data memory as a function of the scatter material distribution and corrects the projection data in respect of the scatter component on the basis of said scatter information.

The invention further relates to a method with scatter correction for projection radiography and a method for obtaining scatter information.

BACKGROUND OF INVENTION

An apparatus and methods of this kind are known from U.S. Pat. No. 6,104,777 A.

The scatter produced in the object under examination (breast), the intensity of which may almost attain the order of magnitude of the direct, unscattered, image-producing primary radiation, results in image quality impairment by reducing the contrast, increasing the noise, and ultimately in respect of the image post-processing methods used for differentiating between various types of tissue in the images produced, in particular between glandular and fatty tissue in the breast. For differentiation in respect of two tissue types, techniques using a single energy spectrum, i.e. a single x-ray tube voltage, or the dual energy method using two voltage values are known in mammography. In both cases scatter compensation is required; with the dual energy method this is also because the amount of scatter is different in the two energy spectra.

To reduce scatter, mechanical measures have already been proposed. The use of slit collimators requires mechanical displacement of the slit collimators over the breast measuring field and is therefore time-consuming. Anti-scatter grids not only reduce the scatter, but also the imaging-producing primary radiation. Arguments in favor of dispensing with anti-scatter grids have been ongoing for years. For compression thicknesses of less than 4-5 cm, the dose could even be reduced or the SNR (=signal-to-noise ratio) increased if the grid is removed. On the other hand there are applications in which it is not technically possible to use a grid, e.g. in tomosynthesis.

A large number of computer correction methods have already been proposed. Methods of this kind are known e.g. from M. DARBOUX, J. M. DINTEN: Physical model based scatter correction in mammography. In: Proc. SPIE, Vol. 3032, 1997, pages 405 to 410 and from J. M. DINTEN and J. M. VOLLE: Physical model based restoration of mammographies. In. Proc. SPIE, Vol. 3336, 1998, pages 641 to 650 and in U.S. Pat. No. 6,104,777 A. These are convolution/deconvolution methods in which a scatter intensity distribution is approximated as a convolution of the primary radiation distribution using suitable convolution kernels. In the cited documents an analytical model is thus proposed with which the physical scatter process in the scatter object (breast) is explicitly computed as an integral transformation. However, this explicit analytical representation only describes first-order scatter, not multiple scatter. The intensity distribution of multiply scattered photons is assumed to be a spatially constant background over the detector surface and must be estimated from previously determined tables. The analytical model for calculating just the first-order scatter contribution requires 4-dimensional numerical integrations (3 space coordinates+energy spectrum) for each detector pixel, i.e. it is compute-intensive. Approximations are therefore required in order to reduce the computational complexity. Because of the high computational complexity it is proposed to perform the calculations in advance and tabulate the results.

In addition, W. KALENDER: Monte Carlo calculations of x-ray scatter data for diagnostic radiology. In: Phys. Med. Biol., 1981, Vol. 26, No. 5, pages 835 to 849 describes the use of Monte Carlo methods for simulating radiation propagation in radiography.

SUMMARY OF INVENTION

Proceeding from this prior art, an object of the invention is therefore to specify an apparatus and methods enabling improved scatter correction compared to the prior art to be performed.

This object is achieved by an apparatus and the methods having the features set forth in the independent claims. Advantageous further developments and embodiments are set forth in claims dependent thereon.

With the apparatus and method, the projection images supplied by a detector are analyzed in a processing unit. It is first attempted to approximately determine the scatter material distribution, in mammography typically the proportions of glandular and fatty tissue, of an object under examination. In another processing step, scatter information depending on the scatter material distribution is read out of a data memory. This scatter information can then be used to correct the projection images in respect of the scatter content of said projection images, it being essential that the scatter information read out of the data memory has been determined in advance by a Monte Carlo simulation which takes the multiple interaction of the photons with the object under examination into account.

The basis for the solution described here is optimally correct physical modeling. In contrast to the prior art, modeling is possible which takes a much larger number of details into account, namely in the following respect: the occurrence of multiple scatter and polychromasia and the geometrical relationships, in particular the peculiarities of the scatter distribution at the edges of the objects, can be simulated. During the scatter correction itself, merely table access is required, possibly with subsequent interpolation, and the calculation of the scatter distribution in the detector plane is reduced to 2-dimensional integrations over the detector plane. Despite the relatively simple implementation of the scatter correction, the procedure is not limited to special cases and requires no drastic simplifications or approximations, such as simplified acquisition geometry, monochromatized radiation, simplifications of the physical model or a Taylor development by orders of approximation or similar.

In a preferred embodiment, the scatter material distribution is specifically determined for different regions of the projection image. To perform scatter correction in an image region, the scatter contributions of the surrounding contributions which depend on the specific scatter material distribution are then determined and corrected accordingly. In this way it is possible to take local scatter variations into account.

In another preferred embodiment, in the region of the edges of the object under examination, scatter information which takes the particular geometrical relationships in the region of the object edge into account is used for scatter correction.

The scatter information is preferably obtained under the assumption that the scatter material distribution is homogeneous along the radiation direction. Particularly in the context of mammography, such an assumption only results in slight deviations from the actual scatter distribution.

The specific scatter information associated with an image area can also be calculated under the assumption that the object under examination is also homogeneously structured in the direction perpendicular to the beam, thereby simplifying the calculation of the scatter information.

However, if particularly high accuracy in calculating the scatter information is required, any inhomogeneity perpendicular to the beam direction can be taken into account.

In a preferred embodiment, the scatter material distribution is determined by analyzing the ratio of incident radiation intensity to the unscattered primary radiation in an image region, the values for the primary radiation being ascertained by means of a scatter correction based on the scatter information associated with a characteristic homogeneous scatter material distribution.

The processing steps carried out by the processing unit can also be executed iteratively, the calculated primary radiation components being used to simplify the approximate calculation of the scatter components and thus arrive at improved values for the primary radiation.

The scatter correction does not generally need to be performed at full detector resolution. It may occasionally be sufficient to perform scatter correction at selected grid points and interpolate between the determined scatter correction values at the selected grid points.

BRIEF DESCRIPTION OF THE DRAWINGS

Further advantages and embodiments of the invention will emerge from the following description in which examples of the invention are specifically explained with reference to the accompanying drawings in which:

FIG. 4 shows the breast tissue distribution assumed for calculating a simple scatter beam spread function; and FIG. 5 shows the breast structure assumed for calculating a precise scatter beam spread function.

DETAILED DESCRIPTION OF INVENTION

Figure 1:
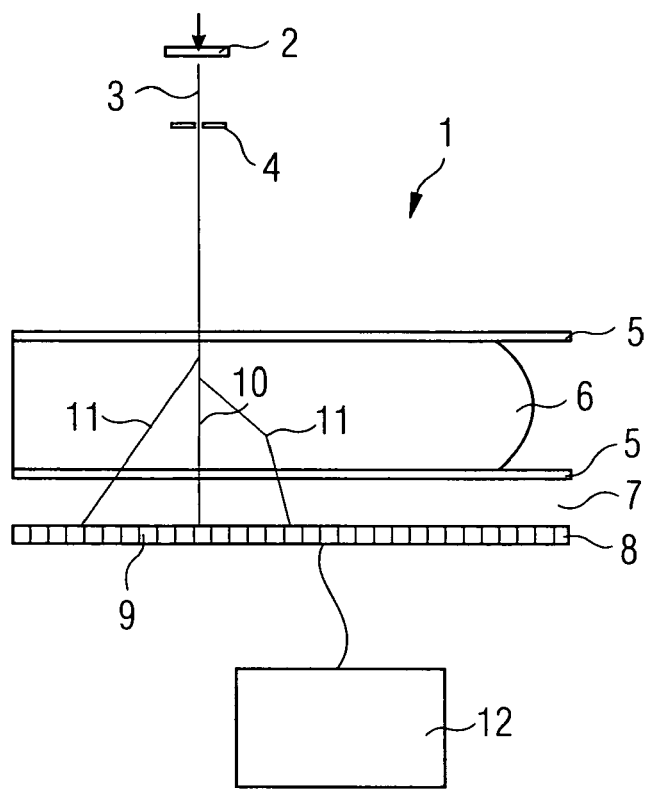
FIG. 1 shows the configuration of a mammography machine in which a breast under examination is compressed between two compression plates and irradiated with x-radiation.

FIG. 1 shows the configuration of a mammography machine 1 in which x-radiation 3 is produced with the aid of a radiation source 2. The divergence of the x-radiation 3 is limited if necessary using a collimator 4 which is shown in FIG. 1 as a single beam diaphragm. However, the collimator 4 can also be contrived such that a plurality of virtually parallel x-ray beams is produced. Such a collimator 4 can be implemented e.g. as an iris diaphragm.

The mammography machine 1 additionally has compression plates 5 between which a breast 6 is compressed. The x-radiation 3 passes through the compression plates 5 and the breast 6 and generally crosses an air gap 7 before the x-radiation 3 is incident on an x-ray detector 8 comprising a plurality of individual detector elements 9, the so-called detector pixels.

The portion of x-radiation 3 passing through the breast 6 without interacting with the breast 6 is known as the primary radiation 10. On the other hand, the portions of x-radiation 3 incident on the x-ray detector 8 after at least one scattering within the breast 6 are referred to as secondary radiation 11.

It should be noted that the term scatter is to be understood as any kind of interaction between the x-radiation 3 and the material of the breast 6 causing a change in the propagation direction of the photons of the x-radiation 3.

Figure 2:
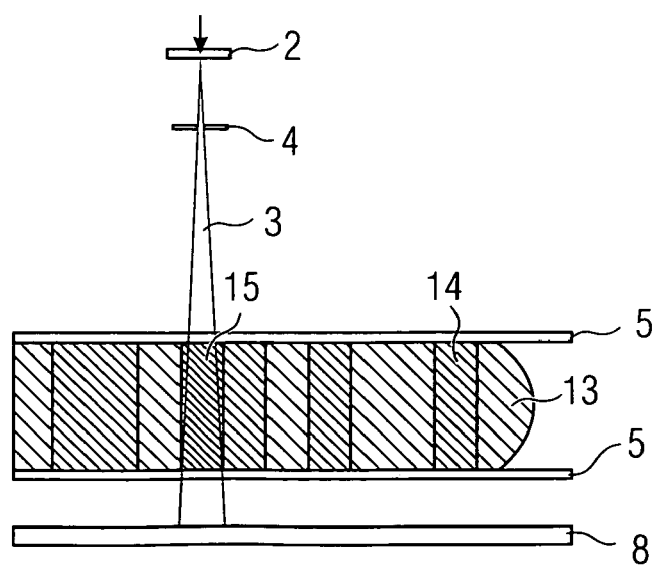
FIG. 2 illustrates a simplified breast structure assumed for calculating the scatter correction.

Since, as mentioned in the introduction, the secondary radiation 11 may considerably distort the structure of the breast 6 imaged by the primary radiation 10, it is advantageous if the secondary radiation 11 can be removed from the projection images of the breast 6 captured by the x-ray detector 8. For this purpose, a processing unit 12 connected downstream of the x-ray detector 8 performs a scatter correction. In order to be able to perform the scatter correction, model assumptions are made concerning the structure of the breast 6. In particular it is assumed that the tissue structure of the breast 6 which is essentially composed of glandular and fatty tissue can be described by a homogeneous tissue distribution along the propagation direction of the x-radiation 3. FIG. 2 accordingly shows different regions 13, 14 and 15 in the breast 6 whose different shadings are designed to illustrate different amounts of fatty and glandular tissue along the propagation direction of the x-radiation 3. In the context of projection radiography, this constitutes a simplification which does not result in major deviations from the actual scatter distribution.

Figure 3:
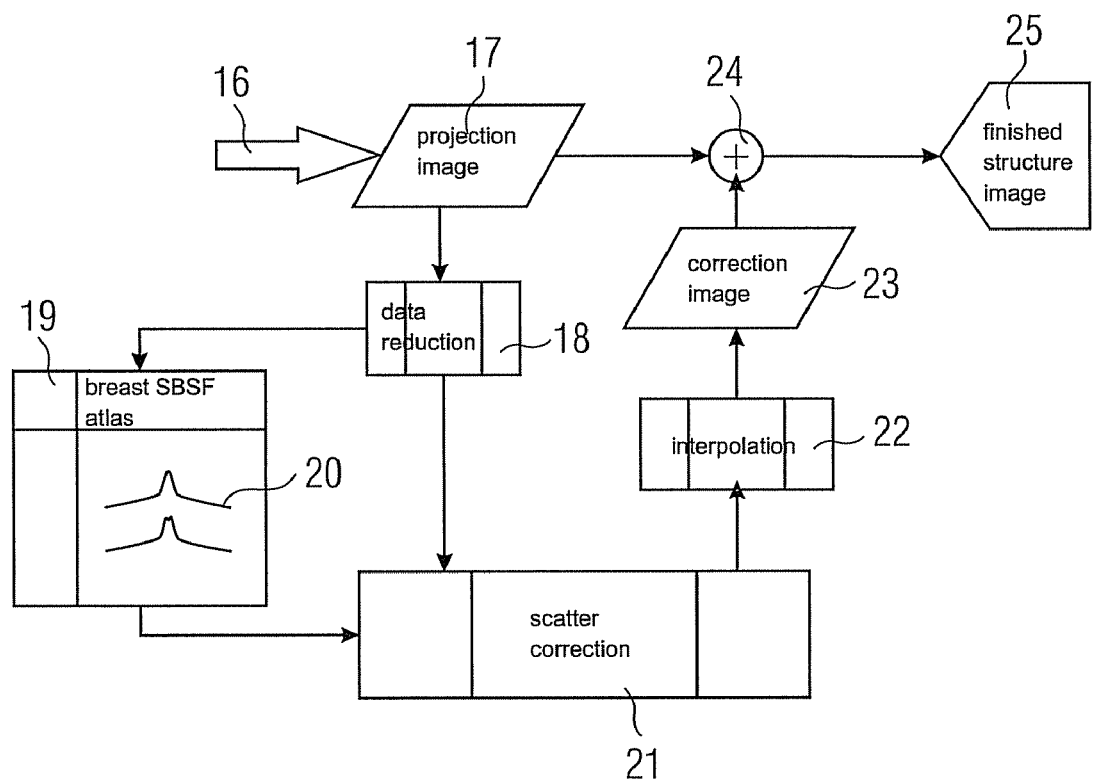
FIG. 3 shows a flowchart of a method performed for scatter correction.

On the basis of this model assumption, the scatter correction can now be performed, the sequence of which is shown in FIG. 3.

After image capture 16, a projection image 17 is present which reproduces the primary radiation 10 and secondary radiation incident on the x-ray detector 8. The projection image 17 undergoes data reduction 18 in which different breast regions 13, 14 and 15 are each assigned specific tissue distributions. In addition, information relating to the geometrical relationships, in particular the edges of the breast 6, are obtained. With the aid of the information obtained in data reduction 18 concerning the physical constitution of the breast 6, a scatter beam spread function (SBSF) 20 assignable to the particular breast region 13, 14 and 15 can be looked up in a breast SBSF atlas 19. Using the SBSFs 20 and an estimate for the primary radiation 10, a scatter correction 21 can then be performed. The correction values generated as part of scatter correction 21 can be directly applied to the projection images 17 if the scatter correction has been calculated for each of the detector pixels 9 of the x-ray detector 8. Because of the minimal scatter variation across the x-ray detector 8, it may be sufficient to perform the scatter correction for selected detector regions. These can be individual grid points or groups of detector pixels 9. The scatter correction for the detector pixels 9 for which no scatter correction has yet been determined can be determined by an interpolation 22 which produces a correction image 23 having the same resolution as the projection image 17. By combination 24 of the projection image 17 and the correction image 23 there is finally produced a finished structure image 25 which preferably contains exclusively the structure of the breast 6 imaged by the primary radiation 10.

The requirements for the radiation correction described here and the associated processing steps will now be described in detail below:

Requirements:

It is firstly assumed that the sensitivity spectrum N(E) critical for imaging is known:

the radiation of the x-ray tubes is polychromatic, the energy spectrum $Q_U(E)$ of the photons emitted as bremsstrahlung at the anode depends on the high voltage U applied with which the electrons are accelerated from the cathode to the anode; the maximum photon energy is then $E_{max}(U)=U(keV/kV)=eU$; however, it is not just the image spectrum that is critical for imaging, but also the transparency of spectral filters W(E) used and the spectral response sensitivity $\eta_D(E)$ of the detector 8. The resulting (normalized) spectral distribution is defined by:

$$N_U(E)=Q_U(E)W(E)\eta_D(E)/c_U. \quad (\#1)$$

With the normalizing factor $$C_U = \int_0^{eU} Q_U(E)W(E)\eta_D(E)\,dE \quad (\#1a)$$

we get $$\int_0^{eU} N_U(E)\,dE = 1$$

It is secondly assumed that—for a given resulting spectral distribution $N_U(E)$ and given breast layer thickness H which is defined by the spacing of the compression plates 5—the attenuation of the detector signal (of primary x-radiation, without scatter) is present in pre-calculated form as a function of the proportion of glandular tissue or fatty tissue(if necessary validated by measurements), i.e. the following function is given in tabular form:

$$F_H(\alpha) = F(\alpha; H, U) \quad (\#2)$$
$$= \int_0^{eU} \exp(-\mu_G(E)x_G - \mu_F(E)x_F)N_U(E)\,dE$$
$$\int_0^{eU} \exp\{\mu_G H(\alpha + \beta(E)(1-\alpha))\}N_U(E)\,dE$$

where

H layer thickness of the breast 6
$\chi_G$ layer thickness, glandular tissue/cm
$\chi_F = H - \chi_G$ layer thickness, fatty tissue/cm
$\rho_G, \rho_F$ density, glandular or fatty tissue [g/cm$^3$]
$b_G = \rho_G \chi_G$ weight per unit area, glandular tissue [g/cm$^2$]
$b_F = \rho_F \chi_F$ weight per unit area, fatty tissue
$\mu_G(E)$ linear attenuation coefficient, glandular tissue/cm$^{-1}$
$\mu_F(E)$ linear attenuation coefficient, fatty tissue/cm$^{-1}$ $$\alpha = \chi_G/H = b_G/(\rho_G H) \quad (\#2a)$$
$$1-\alpha = \chi_F/H = b_F/(\rho_F H) \quad (\#2b)$$
$$\beta(E) = \mu_F(E)/\mu_G(E) \quad (\#2c)$$

it being assumed that the compressed breast 6 completely fills out the layer thickness H between the compression plates 5. As shown in FIG. 4 this condition is no longer met in the region of a few cm near a breast tip 26 and outside in the region of unattenuated radiation. As will be explained in detail below, these image field regions must be dealt with separately as part of a pre-correction, e.g. by suitable extrapolation of the tissue layer thickness H to 0.

For mathematical reasons the logarithmic attenuation signal is more useful than the non-logarithmic attenuation function F in equation (#2):

$$f_H(\alpha) = -\log(F_H(\alpha)) \quad (\#3)$$
$$= -\log\left(\int_0^{eU} \exp\{-\mu_G H(\alpha + \beta(E)(1-\alpha))\}N_U(E)\,dE\right)$$

The function $f_H$ is monotonic and continuous and consequently invertible, e.g. by inverse interpolation. It can therefore be assumed that the inverse function $$f_H^{-1} \quad (\#4)$$

is also available in tabular form.

It is thirdly assumed that the so-called breast SBSF atlas 19 is available, for the method described here is based on knowledge of the relevant SBSFs 20 (scatter beam spread functions). An SBSF 20 describes in each case the spatial intensity distribution of the scatter on the x-ray detector 8 implemented as a flat-panel detector for a thin x-ray beam which penetrates the scatter object (breast) according to FIG. 1 at a predefined location. The SBSF 20 depends on capture parameters and on object parameters.

Capture parameters are, for example, the tube voltage which affects the photon emission spectrum which, moreover, is also dependent on the anode material, the pre-filtering, the air gap, the SID (source-image distance), the collimation, the spectral response sensitivity of the x-ray detector 8 and the presence or absence of an anti-scatter grid.

An object parameter is on the one hand the layer thickness H of the breast 6 and, on the other, the different proportion of glandular or fatty tissue along the propagation direction of the x-radiation 3.

It is assumed that the SBSFs 20 are available for the most important capture and object parameters arising, i.e. that there exists a set of tables created in advance, the so-called breast SBSF atlas 19, which can be used to determine with sufficient accuracy the associated SBSF 20 for the specific capture conditions for each proportion of fatty and glandular tissue (scatter material distribution) along an x-ray beam, e.g. by interpolation in the breast SBSF atlas 19 or by semi-empirical conversions for parameters on which the SBSF is only weakly dependent or for which functional dependencies are known, such as in the case of the SID.

The breast SBSF atlas 19 is created in advance by means of Monte Carlo simulation calculation. Monte Carlo simulation permits adequate modeling of the physical processes of absorption and multiple scattering (predominantly coherent scattering in the lower frequency range in mammography) during passage through the scatter object, in particular the breast 6, taking account of the capture conditions (anode material, filter, voltage, air gap, SID, field size, and possibly anti-scatter grid). This is the major advantage of the Monte Carlo methods over analytical simulation models which are generally limited to single scattering and in which in most cases various simplifications and approximation are also introduced in order to reduce the cost/complexity. The calculation of scatter distributions on the basis of a Monte Carlo simulation will be familiar to the average person skilled in the art and as such is not part of the subject matter of the application.

Description of the Individual Steps:

The scatter correction is subdivided into the following individual steps which can be repeated in an iterative cycle:

0. Empty image calibration and determination of the effective attenuation signal (even a simple general scatter pre-correction being recommended);
1. Determination of the proportion of glandular and fatty tissue;
2. Estimation of the scatter distribution (more accurate SBSF model);
3. Estimation of the primary radiation distribution (scatter correction);
4. Iterative repetition from step 1. or end.

Steps 0. and 1. must be performed for each measuring beam, i.e. for each pixel (j, k), the term pixel being used in the following both for the detector pixels 9 and for detector regions comprising a plurality of detector pixels.

Step 0: $I_0$ calibration and attenuation signal with pre-correction

If $I_0(j, k)$ is the empty image which is identical to the measured intensity distribution in the beam path without scatter object, $I(j, k)$ the measured intensity distribution with scatter object (breast), then the effective attenuation signal for total radiation, i.e. the superposition of primary and secondary (=scattered) radiation, is given by:

$$T(j, k) = I(j, k)/I_0(j, k) \quad (\#5a)$$

In general it will be advisable in respect of step 1. to carry out even here a pre-correction of the scatter background which shall be denoted by $S^{(0)}$. Methods for estimating $S^{(0)}$ are appended below. $S^{(0)}$ can be location-dependent, but is constant in the simplest case. The pre-correction already provides an estimate of the primary attenuation signal (normalized primary intensity)

$$P^{(0)}(j, k) = T(j, k) - S^{(0)} \quad (\#5b)$$

Step 1: Estimation of Specific Tissue Proportions

If $P(j, k)$ is initially assumed to represent only primary radiation without scatter, with equation (#4) and (#3) this yields for the glandular tissue component:

$$\alpha = \alpha(j, k) = f_H^{-1}(-\log(P(j, k))) \quad (190\ 6)$$

and for the glandular tissue weight per unit area [g/cm²]:

$$b_G = \alpha \rho_G H \quad (\#6a)$$

and for the fatty tissue weight per unit area:

$$b_F = (1-\alpha)\rho_F H \quad (\#6b)$$

As the abovementioned assumption does not strictly apply, an iterative procedure is required. This will be explained in greater detail in connection with remarks concerning step 4.

Step 2: Optimally Correct Estimation of the Scatter Distribution Over the Entire Projection Image This step involves several sub-steps:

2.1 Look-Up in the Breast SBSF Atlas

Generation of the SBSF atlas 19 will now be described in further detail.

In step 1, $\alpha(j, k)$ was calculated for each beam to which a pixel (j, k) is assigned. For the calculated value of $\alpha(j, k)$ and H as well as further parameters such as air gap, spectrum and other parameters, the associated SBSF 20 is then generally determined from the breast SBSF atlas 19 by interpolation:

$$SBSF((\lambda_x, \lambda_y); \alpha; H;\ \text{airgap, voltage, filter, detector}, \ldots)$$

SBSF is a two-dimensional function or rather a two-dimensional field (data array) depending on the row and column coordinates on the x-ray detector 8. Each SBSF 20 is focused on a center, namely the particular beam or rather the relevant pixel with the coordinates (0,0) and reduces as a function of distance from the beam center. The distance from the center in both coordinate directions is characterized by an index pair $(\lambda_x, \lambda_y)$. The SBSF 20 is a kind of point or line image function, the beam corresponding to the point or line in reality.

To characterize the interpolation we employ the notation:

$$SBSF^1((\lambda_x, \lambda_y); \alpha)\ \text{with}\ \alpha = \alpha(j, k) \quad (\#7a)$$

This SBSF 20 is to some degree attached to the pixel (j, k) by its center $(\lambda_x, \lambda_y) = (0, 0)$. Therefore, for each beam or each pixel (j, k) we get the SBSF with which that beam or that pixel contributes to the total scatter intensity distribution over the detector surface; this contribution is denoted by $\Delta S$:

$$\Delta S_{(j,k)}(\lambda_x, \lambda_y) = SBSF^1((\lambda_x, \lambda_y); \alpha(j,k)) \quad (\#7)$$

2.2 Integration of the Scatter Distribution Over the Detector

The contributions $\Delta S$ must be integrated over all the pixels.

The SBSFs 20 are normalized to the attenuation=1 of the relevant beam (pixel). For summating all the contributions, it is therefore necessary to multiply by the actual attenuation.

We hold one pixel (j, k) constant and consider all the pixels (j', k') in terms of their contribution to the total scatter in (j, k). The SBSF to some degree attached to the pixel (j', k') then contributes, according to equation (#7), with the contribution:

$$\Delta S_{(j',k')}(\lambda_x, \lambda_y) * P(j', k')\ \text{with}\ \lambda_x = j - j',\ \lambda_y = k - k' \quad (\#8)$$

at the location (j, k).

With (#7) to (#8) we obtain for the scatter at location (j, k):

$$S(j, k) = \sum_{j'} \sum_{k'} \Delta S_{(j',k')}(j - j', k - k') P(j', k') \quad (\#9)$$

This applies to any pixels (j, k) and therefore the total scatter distribution is described by equation (#9).

2.3 Low-Pass Filtering

Because of the multiple scatter processes producing it in the body, the scatter distribution is relatively smooth and therefore exhibits a low-frequency Fourier spectrum. In order to eliminate high-frequency error components induced by the preceding steps, 2-dimensional smoothing is advisable.

Step 3: Scatter Correction

Initially the available data is actually uncorrected, i.e. measurement-based data containing the superposition of primary radiation 10 (direct, unscattered radiation) and secondary radiation 11 (=scatter).

After normalization according to equation (#5a) we have:

$$T = P + S, \quad (\#10)$$

where:

T measured (normalized) distribution of the total radiation
P initially unknown but wanted (normalized) primary radiation 10
S unknown secondary radiation 11, but estimated (normalized) using the proposed model.

Normalization should be understood as division by the intensity distribution $I_0(j, k)$ without scatter object.

Equation (#9) directly yields a subtractive scatter correction:

$$P(j, k) = T(j, k) - S(j, k) \quad (\#11)$$

for estimating the primary radiation distribution.

Another correction which is recommended in cases of a relatively large amount of secondary radiation 11 is multiplicative scatter correction:

$$P = T/(1 + S/P) \quad (\#12)$$

Note that the corrections in equation (#11) and equation (#12) are only approximate and do not provide identical results. For $S/T \ll 1$, however, (#11) becomes (#12).

Step 4: Iteration

In equation (#11) and (#12) the scatter radiation term S, which for its part must be calculated by equation (#9), appears on the right-hand side; however, equation (#9) is defined by means of the (unknown) primary radiation P which for its part appears on the left-hand side of equation (#11) and (#12) and is only to be calculated by one of these equations. P therefore appears both on the left- and right-hand side of equation (#11) and (#12). Such implicit equations must be solved iteratively. We write for S in equation S(#9):

$$S = \underline{S}(P) \quad (\#13a)$$

Equation (#11) is then:

$$P = T - \underline{S}(P) \quad (\#13b)$$

Iteration is performed for the subtractive method as follows:

Start of iteration with pre-correction which will be described in greater detail below:

$$P^{(0)} = T - S^{(0)} \quad (\#5b) = (\#14a)$$

Iteration step:

$$P^{(n+1)} = T - \underline{S}(P^{(n)}), n+1 > 0; \quad (\#14b)$$

For the multiplicative method, the iteration is performed as follows:

Start of iteration with pre-correction which will be described in greater detail below:

$$P^{(0)} = T - S^{(0)} \quad (\#5b) = (\#15a)$$

Iteration step:

$$P^{(n+1)} = P^{(n)} T/(P^{(n)} + \underline{S}(P^{(n)})), n+1 > 0; \quad (\#15b)$$

The sequence of iterations is aborted if the result between step n and n+1 only varies slightly. In many cases even one cycle suffices (n=1).

SNR Improvement by Statistical Estimation: ML and Bayesian Methods

Interestingly the multiplicative correction method (#15b) can be derived from a statistical estimation approach according to the maximum likelihood principle (ML). Although in the relevant technical literature a simple convolutional model is used for the scatter operator $\underline{S}(P)$ in equation (#13a), for example, in A. H. BAYDUSH, C. E. FLOYD: Improved image quality in digital mammography with image processing. In: Med. Phys., Vol. 27, July 2000, pages 1503 to 1508, ML can basically be applied independently of the specific scatter model, particularly also in the case of the scatter model described here.

The feature of a method based on the ML principle is that although the SNR (=signal-to-noise ratio) is usually improved after a few iterations, if the iterations are continued, the noise increases uncontrollably and the SNR deteriorates again. In order to counteract this runaway of the ML algorithm, Bayesian estimation methods are recommended, resulting in algorithms which differ from equation (#15b) in having a stabilizing additional term on the right-hand side. The effect of this additional term on convergence rate, SNR and the compromise between noise and local resolution can be controlled by parameters.

Pre-Corrections

In the previous comments concerning steps 1 and 2.1, equations (#6) and (#7), it was assumed that the compressed breast 6 completely fills out the layer thickness H between the compression plates 5 and that the function $f_H^{-1}$ can be evaluated. As shown in FIG. 4 this condition is no longer fulfilled in the region of a few cm near a breast tip 26 and outside in the region of unattenuated x-radiation 3. These image field regions must be dealt with separately as part of a pre-correction. In the region of unattenuated x-radiation 3 outside the breast 6, the effective attenuation signal according to equation (#5a) must theoretically be =1, but is generally >1 because of the presence of scatter. The difference $$\Delta T(j, k) = 1(j, k)/I_0(j, k) - 1 \quad (\text{if} > 0)$$

must consequently be subtracted as a scatter pre-correction $$S^{(0)} = \Delta T$$

in the image region outside the breast 6.

From the normal image region of the fully compressed breast 6 to the region near the breast tip 26 a suitable extrapolation of the tissue layer thickness from H to 0 must be performed. In this image region, H must therefore generally be assumed to be variable in equations (#2), (#6) and (#7).

If necessary, segmentation into 3 image regions can also be performed as described in K. NYKANEN, S. SILTANEN: X-ray scattering in full field digital mammography. In Med. Phys., Vol. 30(7), July 2003, pages 1864 to 1873.

In the normal image region with constant tissue layer thickness H a scatter pre-correction can look like this: as there has not yet been any evaluation of the tissue proportions (glandular/fatty tissue), initially 100% fat can be assumed. Although because of the lower density of fat (0.92 compared to 0.97 g/cm$^3$ for glandular tissue) the scatter is underestimated, for a 0th-order correction this estimation is significantly better than no correction at all. $\alpha = 0$ is inserted in equation (#7) and the subsequent equations, making the scatter kernel SBSF location-independent, in particular independent of the pixel index (j, k), and equation (#9) is reduced to a genuine convolution.

Equations (#7-#9) are simplified as follows: we omit the index from $\Delta S(j, k)$ and write it as $\Delta S^{(0)}$:

$$\Delta S^{(0)}(\lambda_x, \lambda_y) = SBSF^1((\lambda_x, \lambda_y); \alpha = 0) \quad (\#16a)$$

T according to equation (#5a) must replace P in (#9):

$$S^{(0)}(j, k) = \sum_{j'} \sum_{k'} \Delta S^{(0)}(j - j', k - k') T(j', k') \quad (\#16b)$$
$$= (\Delta S^{(0)} ** T)(j, k)$$

where ** is a 2-dimensional convolution.

The pre-correction then yields according to equation (#5b):

$$P^{(0)} = T - S^{(0)} = T - (\Delta S^{(0)} ** T) \quad (\#16c)$$

Creating the Breast SBSF Atlas

Of interest in the SBSF concept is the distribution of the scatter produced in the scatter body in the detector plane when, as shown in FIG. 4, the (unscattered) primary radiation (i.e. a mini cone beam 27) is focused on a single detector pixel 9. If this is done consecutively for each detector pixel 9 and all the associated SBSFs 20 are summed, the total scatter distribution is obtained for the case where the entire detector surface is illuminated—and not only individual detector pixels 9.

As already described above in connection with the third requirement and step 2, the breast SBSF atlas 19 of the scatter beam spread functions (SBSF) comprises the scatter intensity distributions normalized to the intensity of the primary radiation 10 in the detector pixel 9 (assuming that the mini cone beam 27 is focused on just one pixel 9) as a function of a plurality of different parameter configurations:

$$SBSF((\lambda_x, \lambda_y); \alpha; H; \text{air gap, voltage, filter, detector,} \ldots) \quad (\#17)$$

and also contains the dependency of the x-ray energy spectrum on the tube voltage, pre-filtering, radiation-sensitive detector material, e.g. the type of scintillation crystal, and the dependency on the presence or absence of an anti-scatter grid and where applicable the dependence on the type of anti-scatter grid as well as the dependence on other parameters.

The creation of an SBSF series will now be explained:

First the parameters characterizing the relevant mammography machine 1 are defined: SID, air gap, anode material of the x-ray tubes (and associated emission spectra), detector material, pre-filter material (e.g. compression plates), and other parameters. Then comes the compression thickness H, the voltage, the spectral filters used and other variables, the voltage and if necessary the spectral filter (thickness) generally being modified as a function of the compression thickness H in order to optimize image quality.

For this parameter configuration, the parameter α describing the tissue composition according to equation (#2a) is varied between 0 (fat only) and 1 (glandular tissue only): the calculation using the tried and tested Monte Carlo method produces a set of different SBSFs 20, each α-value being assigned an SBSF 20.

The tissue thickness H is varied between >0 and up to approximately 10 cm and another set of SBSFs 20 is again calculated for each H. The voltage and the spectral filters can also be varied, the variation being linked to H or also independent of H. However, in the latter case multiple variations are possible. In addition, the calculation can be continued for all the parameter combinations.

For calculating the SBSFs 20, simplifications can be performed which are well justified:

Disregarding the beam divergence of the x-radiation 3 due to the cone beam geometry by assuming approximately parallel beam geometry; this is justified in that generally SID>>H; this is achieved in that the SBSF 20 remains location- and pixel-independent for an identical beam configuration; by identical configuration is meant that, for each pixel, the material distribution is the same along the mini cone beam 27 and in the lateral neighborhood.

To improve the statistics for the Monte Carlo method and reduce the computational complexity, pixels approximately an order of magnitude larger (e.g. 1×1 mm² or 2×2 mm²) than the actual detector pixels 9 (<0.1 mm) are used to calculate the SBSFs 20; this is justified by the low-frequency Fourier spectrum of the spatial scatter distribution.

The succession of fatty and glandular tissue is replaced by a mixture; although the scatter depends (for the same weight per unit area and path length) on whether the denser tissue is nearer the x-ray detector 8 or nearer the radiation source 2, according to J. M. DINTEN and J. M. Volle: Physical model based restoration of mammographies. In Proc. SPIE, Vol. 3336, 1998, 641-650, the differences occurring under mammographic conditions can be disregarded.

Advantages

The solution proposed here has the following advantages:

If required, the method can be incorporated in existing mammography machines without mechanical reconstruction.

Moreover it is a method which on the one hand shares the adequacy of physical modeling using the Monte Carlo method, but on the other hand—because all the time-consuming calculations are carried out in advance where possible and the necessary data is stored in tables—ultimately involves relatively low computational complexity for the scatter correction.

The modeling accuracy of the scatter correction described here is essentially greater than that of the known (analytical) physical models, as a number of simplifying assumptions and approximations can be dispensed with.

The possibilities of the scatter correction proposed here go far beyond the possibilities of the long known convolution/deconvolution methods. Disregarding the specific technical embodiment of the method and looking at it from a mathematical standpoint, the method can be regarded in the mathematical sense as a generalization of the long known convolution/deconvolution method. On the one hand, by using approximations and dispensing with accuracy, it can be categorized as method of this type and then shares its advantages, such as the possibility of using the so-called FFT (=Fast Fourier Transformation). On the other hand, however, the method described here can also be extended in terms of SNR improvement, e.g. by extending the iterative multiplicative algorithm in the direction of statistical Bayesian estimation.

In this context it should be re-emphasized that only pre-calculation of the SBSFs 20 enables the method described here to be performed in full generality.

EXAMPLES

Example 1

In this example, scatter correction is performed, as described above with equations (#5)-(#9) and (#13)-(#15), using homogeneous location-dependent scatter beam spread functions 20 (=SBSF). For creating said scatter beam spread functions 20 it is assumed by way of simplification that the tissue distribution characterized by the proportion α(j, k) of glandular tissue along the beam leading from the source to the detector pixel continues in a constantly homogeneous manner according to FIG. 4 at right angles to the beam, i.e. parallel to the compression plates 5. It is therefore assumed with respect to the scatter contribution of the beam in the pixel (j, k) that the tissue composition in the lateral neighborhood of the beam does not vary abruptly. Although this is no longer relevant at the edge of the breast, special treatment could be provided there.

Note, however, that the actual location-dependent inhomogeneity of the tissue composition is allowed for by a specifically different amount of glandular tissue $\alpha(j', k')$ for each pixel $(j', k')$ and a specific scatter contribution dependent thereon. The SBSFs 20 are therefore generally different for each pixel.

Example 1a

In this example 1a the method is essentially performed as in example 1.

However, the following simplifications are made:

For each pre-specified layer thickness and the other parameters such as voltage and pre-filtering, a common SBSF 20 is used for all the pixels. In this case the SBSF 20 is therefore selected on a location-independent basis. The selection can be made, for example, by suitable averaging over the tissue compositions present. $\Delta S$ in equation (#7) and (#9) then becomes independent of the pixel index $(j, k)$; the double index $(j, k)$ can—similarly as in equations (#16a) to (#16c)—be omitted.

The important feature is that the integral in equation (#9) becomes a genuine convolution which can be efficiently executed by FFT (=Fast Fourier Transformation).

Example 1b

In this example 1b the method is likewise performed essentially as in example 1.

In this case, however, a uniform convolution kernel (for all the layer thicknesses) is used for the scatter calculation. The fact that for a small layer thickness relatively less scatter is produced than for a large layer thickness must be taken into account by means of scaling factors which are a function of the layer thickness and other parameters such as voltage and filtering.

Approximately the same computational complexity is necessary for example 1b as for example 1a. On the other hand, much less memory space is required for storing the breast SBSF atlas 19 in this example.

Notes on Examples 1a and 1b

In general the simplified examples 1a and 1b share the characteristic that the convolutional models for the scatter can be inverted using the Fourier transformation. This is known as deconvolution. The examples described here differ from the conventional deconvolution methods in using one or more scatter beam spread functions 20 obtained in advance by Monte Carlo simulation.

With regard to performing deconvolution, reference is made to a publication by J. A. SEIBERT and J. M. BOONE: X-ray scatter removal by deconvolution. In Med.Phys., Vol. 15, 1988, pages 567 to 575. Reference is also made to the more recent publication P. ABBOTT et al: Image deconvolution as an aid to mammographic artifact identification I: basic techniques. In: Proc.SPIE, Vol. 3661, 1999, pages 698 to 709 which deals with deconvolution using regularization techniques for noise suppression. Another deconvolution method with thickness-dependent convolution is described in D. G. TROTTER et al: Thickness-Dependent Scatter-Correction Algorithm for Digital Mammography. In: Proc. SPIE, Vol. 4682, 2002, pages 469 to 478. In this method an iteration with relaxation is performed.

Example 2

In this example the method is essentially performed as in example 1, but employing scatter beam spread functions 20 which have been calculated for an inhomogeneous medium.

FIG. 5, for example, illustrates the case where a breast region 28 has a different composition from that of a surrounding breast region 29.

This enables it to be taken into account that the SBSF 20 depends not only on the tissue composition along the mini cone beam 27 supposedly focused on the detector pixel 27 but also on the tissue composition in the lateral neighborhood into which photons are scattered and can be further scattered again in the direction of the pixel. However, the effective extent of the lateral neighborhood is not very large because of the average free path length <~2 cm of photons in the mammography energy range between about 20 and 40 keV. It would therefore suffice to assume the tissue composition to be homogeneous in a lateral half space, but generally different from the mini cone beam 27. The allowance for inhomogeneous SBSFs 20 with differences between beam and neighborhood might be relevant particularly at the breast edge.

This example therefore constitutes a generalization of the above-described examples 1, 1a and 1b, as in this case the SBSFs 20 depend not only on a tissue parameter $\alpha$, but also on a surrounding tissue parameter $\gamma$ to be newly introduced. In this case the breast SBSF atlas 19 would therefore have an additional dimension.

For the sake of clarity, the following table compares the different characteristics of examples 1, 1a, 1b and 2:

| SBSF | Examples | | | |
|---|---|---|---|---|
| | 1 | 1a | 1b | 2 |
| thickness-dependent | + | + | − | + |
| location- (pixel-)dependent | + | − | − | + |
| inhomogeneous | − | − | − | + |

Example 3

The method described here can also be applied to so-called dual energy methods which will be known to the average person skilled in the art. With the so-called dual energy method, which is used primarily in mammography or in bone densitometry, images are recorded simultaneously using two different energy spectra. The recordings using different energy spectra are provided by two different voltages and if possible also different spectral filtering so that the spectral regions effectively corresponding to the two measurements overlap one another as little as possible. By means of a computational process which is essentially based on the solution of a generally nonlinear system of two equations assigned to the two spectra, finer tissue differentiation can be achieved compared to a recording using one energy spectrum. For computation to be successful, the scatter components must be eliminated as much as possible, as otherwise the artifacts induced by the scatter components are in some circumstances stronger than the actual tissue image.

Because of the differences in scatter for the two spectra, effective scatter correction is therefore critically important for the quality of the dual energy method.

The proposed scatter correction method can also be used in this context. The geometrical parameters are identical for the two recordings, but the spectrally dependent parameters are different.

The correction must be carried out for each of the two recordings according to the described formula, the only difference being that different SBSFs 20 must be used according to the different spectra.

The invention claimed is:

1. A projection radiography apparatus comprising:
   a radiation source that emits radiation to an object corresponding to a portion of a patient under medical examination having scatter material causing a scatter portion;
   a radiation detector that supplies projection data;
   a data memory that stores information about scattering, the information determined by Monte Carlo simulations which calculate the interactions of photons with scatter material for different distributions of scatter material; and
   a processing unit configured to:
   generate a first projection image from the projection data based on a combination of primary radiation and secondary radiation incident on the detector;
   perform a data reduction on the first projection image in which multiple different regions of the object are assigned specific tissue distributions;
   determine a scatter material distribution of the object based upon the projection data supplied by the detector, including assigning a scatter beam spread function to each of the multiple regions of the object;
   obtain scatter information from the data memory which corresponds to each assigned scatter beam spread function;
   use the scatter information to determine, with the scatter beam spread function, a scatter beam correction corresponding to contribution of the secondary radiation in the projection data; and
   generate a corrected image of the object based on a combination of the first projection image and the scatter beam correction, so that a portion of the secondary radiation present in the projection data is removed in the process of generating the corrected image.

2. The projection radiography apparatus as claimed in claim 1, comprising scatter distributions as scatter information, the scatter distributions each describing the scatter-induced distribution of radiation to adjacent image regions of the object, the adjacent image regions each adjoining an image region to which radiation is directly directed.

3. The projection radiography apparatus as claimed in claim 1, wherein the scatter distributions are scalable based upon the intensity of unscattered primary radiation incident on the detector.

4. The projection radiography apparatus as claimed in claim 1, wherein the processing unit evaluates scatter information specific to the particular scatter material distribution for different image regions of a projection image.

5. The projection radiography apparatus as claimed in claim 1, wherein the processing unit determines a scatter distribution in an image region of a projection image by calculating and adding the scatter contributions of surrounding image regions for each image region.

6. The projection radiography apparatus as claimed in claim 1, wherein the processing unit determines a scatter distribution in an image region of the projection image by convolving a primary radiation distribution with a scatter distribution.

7. The projection radiography apparatus as claimed in claim 1, wherein the processing unit determines unscattered primary radiation by solving the implicit equation $P+S(P)=T$, where P is the distribution of unscattered primary radiation, S(P) is the secondary radiation distribution dependent on the unscattered primary radiation and T is the measured total radiation distribution in projection images.

8. The projection radiography apparatus as claimed in claim 1, wherein the processing unit estimates the amount of scatter contained in a projection image to achieve a first approximate determination of the scatter material distribution of the object under examination, wherein the estimation is based upon scatter information associated with a typical scatter material distribution.

9. The projection radiography apparatus as claimed in claim 1, wherein the processing unit performs the processing steps iteratively.

10. The projection radiography apparatus as claimed in claim 1, wherein the scatter information is calculated under the assumption of a homogeneous scatter material distribution in a beam direction.

11. The projection radiography apparatus as claimed in claim 1, wherein scatter information is stored in the data memory based upon an outer contour of the object under examination.

12. The projection radiography apparatus as claimed in claim 1, wherein the scatter information is stored in the data memory, and the stored scatter information is based upon an assumption of a homogeneous scatter material distribution perpendicular to a beam direction.

13. The projection radiography apparatus as claimed in claim 1, wherein the scatter information stored in the data memory is determined based upon the assumption of an inhomogeneous scatter material distribution in directions perpendicular to a beam direction.

14. The projection radiography apparatus as claimed in claim 1, wherein the scatter information stored in the data memory depends on parameters of the radiation source.

15. The projection radiography apparatus as claimed in claim 1, wherein the detector has individual elements and the processing unit determines the scatter portion at selected grid points and determines correction values for individual detector elements by interpolation between the grid points.

16. The projection radiography apparatus as claimed in claim 1, wherein the object under examination is compressed in a compression device and wherein the processing unit determines a path length of the radiation through the object under examination based upon the physical configuration of the surfaces of the compression device facing the object under examination.

17. The projection radiography apparatus as claimed in claim 1, wherein the apparatus is a mammography machine.

18. The projection radiography apparatus of claim 1 wherein the processing unit generates the corrected image by generating correction data corresponding to a correction image and combining the correction data with the projection data.

19. The projection radiography apparatus of claim 1 wherein the radiation detector has a plurality of pixels and wherein the processing unit calculates a scatter correction for each of the detector pixels and correction values generated as part of the scatter beam correction are directly applied to the first projection image to generate the corrected image.

* * * * *